United States Patent
Ogihara et al.

(10) Patent No.: US 10,980,405 B2
(45) Date of Patent: Apr. 20, 2021

(54) IMAGING DEVICE AND ENDOSCOPE

(71) Applicant: OLYMPUS CORPORATION, Tokyo (JP)

(72) Inventors: Tomoharu Ogihara, Higashimurayama (JP); Fumiyuki Okawa, Tama (JP); Keisuke Tsutsui, Kawaguchi (JP); Keisuke Ogawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 334 days.

(21) Appl. No.: 16/220,113

(22) Filed: Dec. 14, 2018

(65) Prior Publication Data

US 2019/0117053 A1 Apr. 25, 2019

Related U.S. Application Data

(63) Continuation of application No. PCT/JP2017/031995, filed on Sep. 5, 2017.

(30) Foreign Application Priority Data

Nov. 14, 2016 (JP) ................................ 2016-221155

(51) Int. Cl.
*A61B 1/04* (2006.01)
*A62B 1/04* (2006.01)
(Continued)

(52) U.S. Cl.
CPC .......... *A61B 1/045* (2013.01); *A61B 1/00009* (2013.01); *A61B 1/05* (2013.01);
(Continued)

(58) Field of Classification Search
CPC ....... A61B 1/045; A61B 1/00009; A61B 1/05; A61B 1/00096; G02B 23/2407;
(Continued)

(56) References Cited

U.S. PATENT DOCUMENTS

| 8,896,680 B2 | 11/2014 | Okawa et al. |
| 9,591,233 B2 | 3/2017 | Adachi |
| 2013/0265403 A1* | 10/2013 | Okawa ................... A61B 1/045 |
| | | 348/76 |

FOREIGN PATENT DOCUMENTS

| JP | 2003-038433 A | 2/2003 |
| JP | 2015-192695 A | 11/2015 |

(Continued)

OTHER PUBLICATIONS

International Search Report dated Nov. 14, 2017 issued in International Application No. PCT/JP2017/031995.

*Primary Examiner* — William Choi
(74) *Attorney, Agent, or Firm* — Scully, Scott, Murphy & Presser, P.C.

(57) ABSTRACT

An imaging device includes: a pixel unit including a plurality of pixels that are arranged in a two-dimensional matrix, each pixel being configured to generate an imaging signal corresponding to an amount of light received and output the image signal; an A/D converter configured to conduct A/D conversion on the imaging signal generated by the pixel unit or on a drive power for driving the pixel unit, to generate a digital signal and output the digital signal to an external unit; a switch that is capable of switching a connection of the A/D converter to the pixel unit or a transmission line for transmitting the drive power; and a first controller configured to control the switch to connect the A/D converter to the transmission line in predetermined timing to cause the A/D converter to output a voltage value of the drive power to the external unit.

10 Claims, 6 Drawing Sheets

(51) Int. Cl.
    *A61B 1/045*         (2006.01)
    *G02B 23/24*         (2006.01)
    *A61B 1/05*          (2006.01)
    *H04N 5/225*        (2006.01)
    *H04N 5/335*        (2011.01)
    *A61B 1/00*          (2006.01)

(52) U.S. Cl.
    CPC ..... *G02B 23/2407* (2013.01); *G02B 23/2423* (2013.01); *G02B 23/2469* (2013.01); *G02B 23/2484* (2013.01); *H04N 5/225* (2013.01); *H04N 5/335* (2013.01); *A61B 1/00096* (2013.01)

(58) Field of Classification Search
    CPC ............ G02B 23/2423; G02B 23/2469; G02B 23/2484; H04N 5/225; H04N 5/335
    USPC ...................................... 600/109; 348/65, 74
    See application file for complete search history.

(56) References Cited

FOREIGN PATENT DOCUMENTS

| WO | 2013/042647 A1 | 3/2013 |
|---|---|---|
| WO | 2016/027487 A1 | 2/2016 |

\* cited by examiner

IMAGING DEVICE AND ENDOSCOPE

CROSS REFERENCES TO RELATED APPLICATIONS

This application is a continuation of PCT international application Ser. No. PCT/JP2017/031995 filed on Sep. 5, 2017 which designates the United States, incorporated herein by reference, and which claims the benefit of priority from Japanese Patent Applications No. 2016-221155, filed on Nov. 14, 2016, incorporated herein by reference.

BACKGROUND

1. Technical Field

The present disclosure relates to an imaging device configured to be inserted into a subject to capture the inside of the body of the subject and to an endoscope.

2. Related Art

In the related art, there is a known technology in which an imaging device, such as CCD (Charge Coupled Device) or CMOS (Complementary Metal Oxide Semiconductor), is disposed at the distal end of an insertion portion of an endoscope and a processor supplies drive signals and power-supply voltage through a signal cable having a length of about several meters (see Japanese Laid-open Patent Publication No. 2003-38433). According to this technology, the processor is provided with monitoring circuitry that detects a substrate voltage of the imaging device and, in accordance with a detection result detected by the monitoring circuitry, the timing for tuning on the power of the imaging device and the timing for supplying a drive signal are synchronized so that the imaging device is operated in a stable manner.

SUMMARY

In some embodiments, an imaging device includes: a pixel unit including a plurality of pixels that are arranged in a two-dimensional matrix, each pixel being configured to generate an imaging signal corresponding to an amount of light received and output the image signal; an A/D converter configured to conduct A/D conversion on the imaging signal generated by the pixel unit or on a drive power that is an external input and that is used for driving the pixel unit, to generate a digital signal and output the digital signal to an external unit; a switch that is capable of switching a connection of the A/D converter to the pixel unit or a transmission line for transmitting the drive power; and a first controller configured to control the switch to connect the A/D converter to the transmission line in predetermined timing to cause the A/D converter to output a voltage value of the drive power to the external unit.

In some embodiments, an imaging device includes: a pixel unit including a plurality of pixels that are arranged in a two-dimensional matrix, each pixel being configured to generate an imaging signal corresponding to an amount of light received and output the image signal; an A/D converter configured to conduct A/D conversion on the imaging signal generated by the pixel unit or on a drive power that is an external input and that is used for driving the pixel unit, to generate a digital signal and output the digital signal to an external unit; and a first controller configured to cause the A/D converter to output a voltage value of the drive power to the external unit in predetermined timing. The A/D converter includes: a first A/D converter that is connected to the pixel unit, the first A/D converter being configured to conduct A/D conversion on the imaging signal to generate a digital imaging and output the digital imaging signal to the external unit; a second A/D converter that is connected to a transmission line for transmitting the drive power, the second A/D converter being configured to conduct A/D conversion on the drive power to output a digital voltage value of the drive power to the external unit; and a switch that is connected to the first A/D converter and the second A/D converter, the switch being configured to connect an output of any one of the first A/D converter and the second A/D converter to an external transmission line for transmitting a signal to the external unit, and the first controller is configured to control the switch to connect the second A/D converter to the external transmission line in predetermined timing.

In some embodiments, an endoscope includes: the above-mentioned imaging device; a power source configured to adjust a voltage of an external power input from a processor to be supplied as the drive power; and a second controller that controls a voltage of the drive power to be adjusted by the power source, based on the voltage value.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
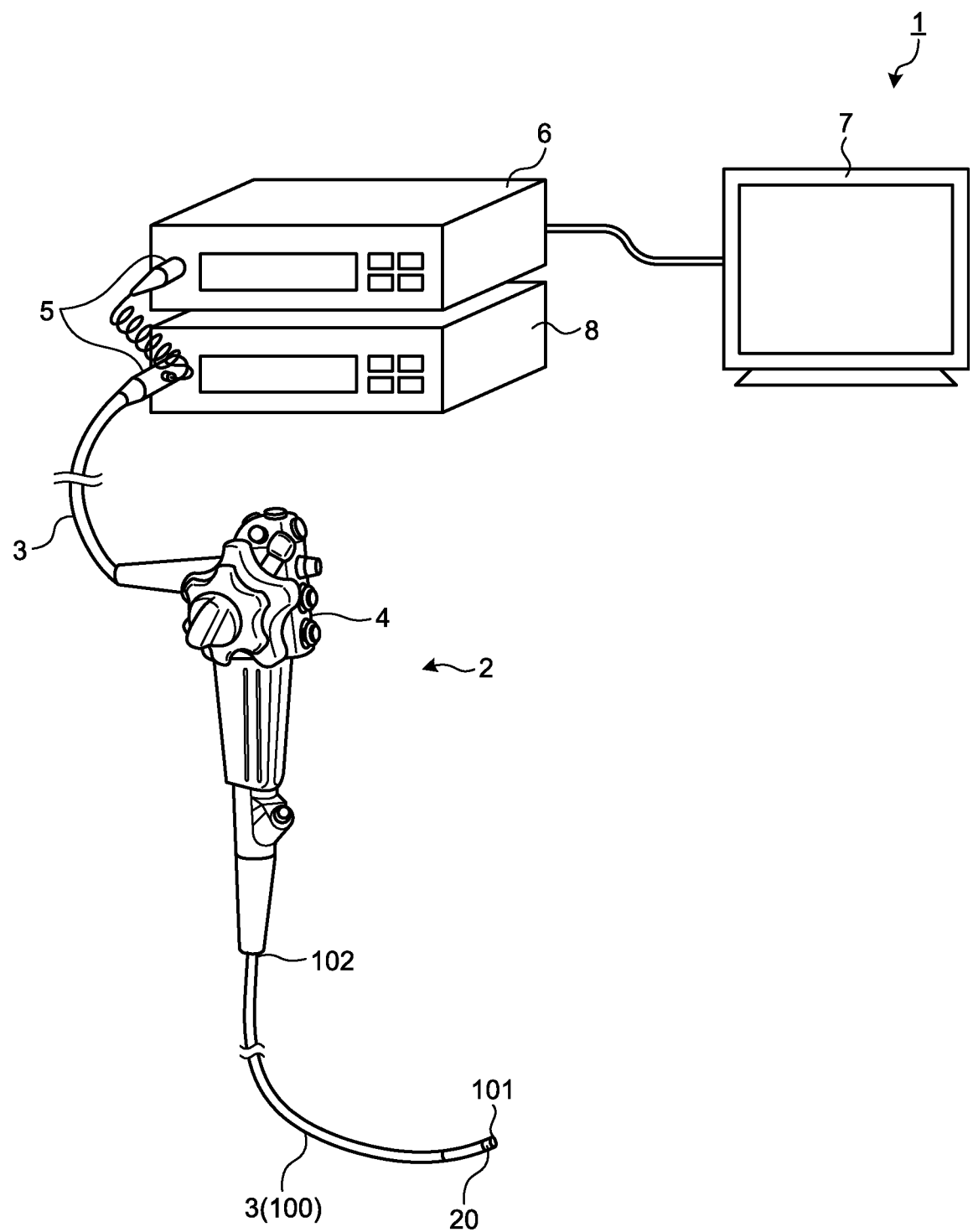
FIG. 1 is a diagram that schematically illustrates the overall configuration of an endoscope system according to a first embodiment of the present disclosure.

An endoscope system including an imaging device is explained below as aspects (hereafter, referred to as "embodiments") for implementing the present disclosure. Furthermore, the embodiments are not a limitation on the present disclosure. Furthermore, the same components are attached with the same reference numeral in description of the drawings. Furthermore, it should be noted that the drawings are schematic and the relation between members in thickness or width, the proportion between members, and the like, differ from reality. Moreover, the drawings contain different part in dimension or proportion from one another.

First Embodiment

Configuration of the Endoscope System

FIG. 1 is a diagram that schematically illustrates the overall configuration of an endoscope system according to a first embodiment of the present disclosure. An endoscope system 1 illustrated in FIG. 1 includes an endoscope 2, a transmission cable 3, a connector unit 5, a processor 6, a display device 7, and a light source device 8.

The endoscope 2 inserts an insertion portion 100, which is part of the transmission cable 3, into the body cavity of a subject to capture the inside of the body of the subject and outputs an imaging signal to the processor 6. In the endoscope 2, an imaging device 20 that captures the inside of the body is provided at one end side of the transmission cable 3 and at the side of a distal end portion 101 of the insertion portion 100 to be inserted into the body cavity of the subject, and an operating unit 4 that receives various operations for the endoscope 2 is coupled to the side of a proximal end portion 102 of the insertion portion 100. The imaging device 20 is formed by using CCD, CMOS, or the like, and it is coupled to the connector unit 5 with the transmission cable 3 through the operating unit 4. Imaging signals captured by the imaging device 20 are transmitted through the transmission cable 3 having a length of, for example, several meters and are output to the connector unit 5.

The transmission cable 3 couples the endoscope 2 to the connector unit 5 and couples the endoscope 2 to the light source device 8. The transmission cable 3 is configured by using light guide, such as transmission lines or optical fibers, or the like.

The connector unit 5 is coupled to the endoscope 2, the processor 6, and the light source device 8 so as to execute predetermined signal processing on imaging signals output from the coupled endoscope 2 and output them to the processor 6.

The processor 6 executes predetermined image processing on imaging signals output from the connector unit 5 and controls the overall endoscope system 1 in an integrated manner.

The display device 7 displays an image corresponding to the imaging signal on which the processor 6 has executed image processing. The display device 7 presents various types of information related to the endoscope system 1.

The light source device 8 supplies illumination light for irradiation by the endoscope 2. The light source device 8 is configured by using, for example, a halogen lamp, LED (Light Emitting Diode), or the like. The light source device 8 supplies illumination light to the endoscope 2 under the control of the processor 6.

Figure 2:
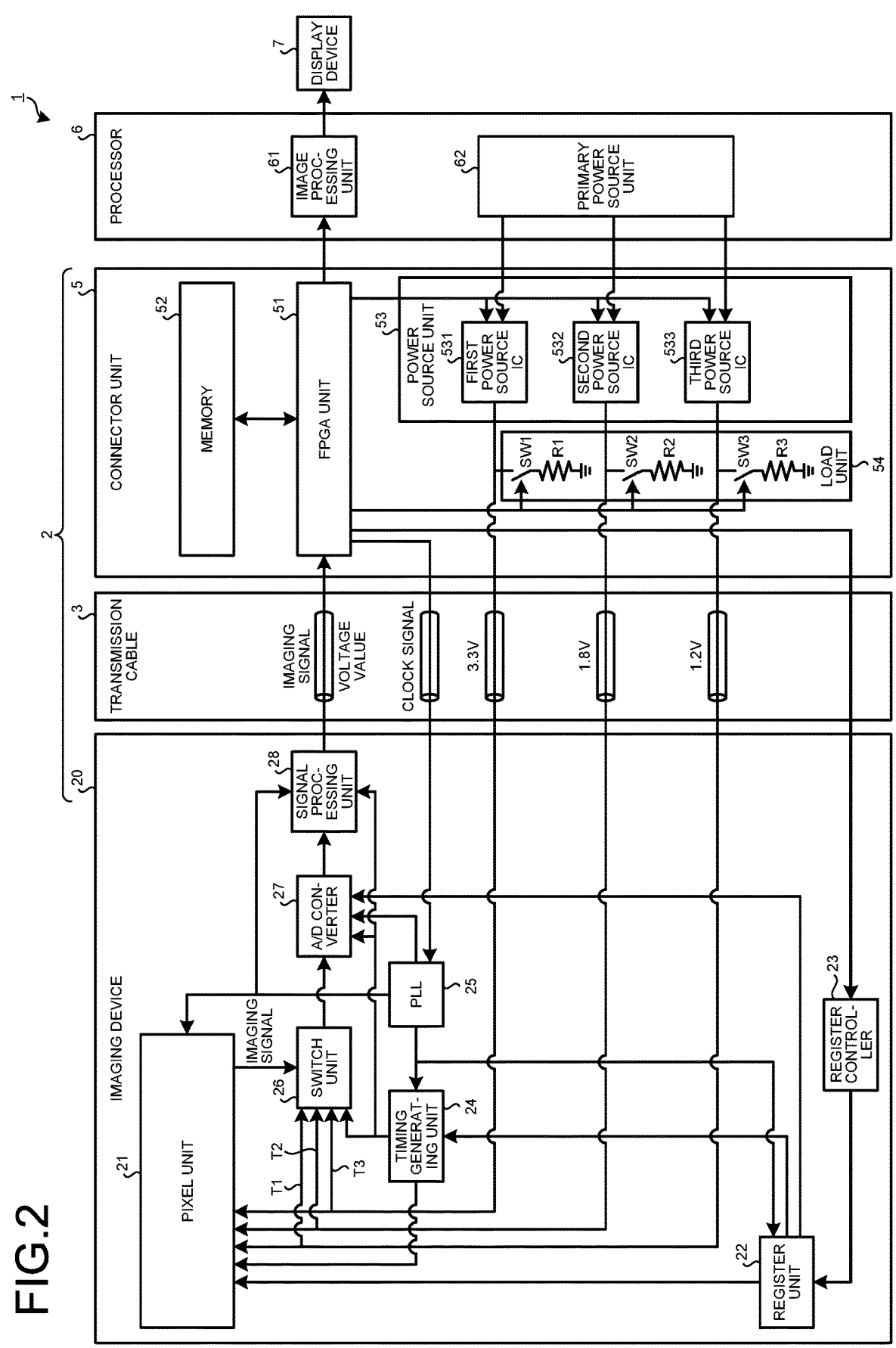
FIG. 2 is a block diagram that illustrates a function of a relevant part of the endoscope system according to the first embodiment of the present disclosure.

FIG. 2 is a block diagram that illustrates a function of a relevant part of the endoscope system 1. With reference to FIG. 2, an explanation is given of the detailed configuration of each unit in the endoscope system 1 and the path of an electric signal in the endoscope system 1. Here, in FIG. 2, the primary power source of the processor 6 described later supplies a drive power to each unit in the endoscope system 1; for simplified explanation, however, an explanation is omitted except for the primary area according to the present embodiment.

Configuration of the Imaging Device

First, the configuration of the imaging device 20 is explained. As illustrated in FIG. 2, the imaging device 20 includes a pixel unit 21, a register unit 22, a register controller 23, a timing generating unit 24, a PLL (Phase Locked Loop) 25, a switch unit 26, an A/D converter 27, and a signal processing unit 28.

The pixel unit 21 includes a plurality of pixels arranged in a two-dimensional matrix. Each pixel generates an electric signal corresponding to an amount of light received as an imaging signal and outputs the imaging signal to the switch unit 26.

The register unit 22 stores various programs for driving the pixel unit 21 and various types of information related to the imaging device 20. Under the control of the register controller 23, the register unit 22 designates a pixel from which an imaging signal is to be read and causes the pixel unit 21 to output it to the switch unit 26. Furthermore, the register unit 22 outputs various programs for driving the timing generating unit 24 and the A/D converter 27. Moreover, the register unit 22 outputs various programs to each component based on a clock signal input from the PLL 25.

The register controller 23 controls driving of the register unit 22 based on a control signal input from the connector unit 5 described later.

The timing generating unit 24 controls driving of the pixel unit 21, the switch unit 26, the A/D converter 27, and the signal processing unit 28 based on a clock signal input from the PLL 25. Furthermore, the timing generating unit 24 controls the switch unit 26 such that the A/D converter 27 is connected to transmission lines T1 to T3 for transmitting drive powers input from an external unit in predetermined timing, thereby causing the A/D converter 27 to output voltage values of the drive powers to an external unit. Specifically, the timing generating unit 24 controls the switch unit 26 such that the A/D converter 27 is connected to the transmission lines T1 to T3 for transmitting drive powers during a blanking period of the pixel unit 21. According to the present embodiment, the timing generating unit 24 functions as a first controller.

The PLL 25 multiplies a clock signal input from the connector unit 5 by 1/N to adjust and output a high-accuracy clock signal that may correspond to each component included in the imaging device 20. Specifically, the PLL 25 outputs adjusted clock signals to the pixel unit 21, the register unit 22, the timing generating unit 24, and the A/D converter 27.

The switch unit 26 switches the connection of the A/D converter 27 to the pixel unit 21 or the transmission lines T1 to T3 based on a clock signal input from the timing generating unit 24. One end of the switch unit 26 is connected to the A/D converter 27, and the other end of the switch unit 26 is connected to the pixel unit 21 or the transmission lines T1 to T3 (the transmission cable 3) for transmitting drive powers input from an external unit. Specifically, the switch unit 26 connects the A/D converter 27 to the pixel unit 21 during an imaging period of the imaging device 20 and connects the A/D converter 27 to the transmission lines T1 to T3 (drive voltages of 1.2 V, 1.8 V, and 3.3 V) for transmitting drive powers during a blanking period of the imaging device 20. The switch unit 26 is implemented by using a semiconductor switch, such as PMOS or NMOS, a mechanical switch, or the like. Furthermore, the switch unit 26 includes a plurality of switch units where each switch unit corresponds to each one of the transmission lines T1 to T3.

The A/D converter 27 conducts A/D conversion on the imaging signal generated by the pixel unit 21 or on the drive power for driving the pixel unit 21, input from an external unit, to generate a digital imaging signal and outputs the digital imaging signal to an external unit. The A/D converter 27 conducts A/D conversion on the imaging signal input from the switch unit 26 to convert an analog imaging signal into a digital imaging signal and outputs the digital signal to the signal processing unit 28. Furthermore, the A/D converter 27 conducts A/D conversion for sampling in predetermined timing on a drive power input from the switch unit 26 to generate a voltage value (monitored value) of the drive power and outputs the voltage value to the signal processing unit 28. Furthermore, the A/D converter 27 includes a plurality of A/D converters where each A/D converter is provided for every predetermined vertical line (e.g., every 5 lines or every 10 lines) in the pixels constituting the pixel unit 21.

The signal processing unit 28 conducts modulation processing for conversion into a predetermined number of bits (e.g., 8 bits to 10 bits) or parallel/serial conversion processing for parallel/serial conversion on the imaging signal input from the A/D converter 27 and outputs the imaging signal to the connector unit 5.

Configuration of the Connector Unit

Next, a configuration of the connector unit 5 is explained. The connector unit 5 includes an FPGA (Field Programmable Gate Array) unit 51, a memory 52, a power source unit 53, a load unit 54, a first switch SW1, a second switch SW2, and a third switch SW3.

The FPGA unit 51 reads various programs from the memory 52 to control driving of the imaging device 20 and perform predetermined signal processing on the imaging signal output from the imaging device 20 and output the imaging signal to the processor 6. Here, the predetermined signal processing is serial/parallel conversion processing, gain-up processing, and the like. Furthermore, the FPGA unit 51 controls a second switch unit described later such that the load unit 54 is connected to the transmission lines T1 to T3 for transmitting drive powers during a blanking period of the imaging device 20 from which the imaging signal is output. Here, according to the present embodiment, the FPGA unit 51 functions as the second controller.

The memory 52 stores various programs executed by the FPGA unit 51 and parameters for image processing executed. The memory 52 is configured by using a nonvolatile memory, or the like.

The power source unit 53 adjusts a drive voltage input from the primary power source of the processor 6 described later to a predetermined voltage and feeds it to the transmission cable 3. Specifically, the power source unit 53 adjusts different drive powers input from the primary power source of the processor 6 described later to predetermined voltages (e.g., drive voltages of 1.2 V, 1.8 V, and 3.3 V) and outputs them to the imaging device 20. The power source unit 53 includes a first power source IC 531, a second power source IC 532, and a third power source IC 533.

Under the control of the FPGA unit 51, the first power source IC 531 adjusts a voltage of a drive power input from the primary power source of the processor 6 described later to, for example, approximately a drive voltage of 3.3 V±3% and applies it to the transmission cable 3, thereby feeding the drive power to the imaging device 20.

Under the control of the FPGA unit 51, the second power source IC 532 adjusts a voltage of a drive power input from the primary power source of the processor 6 described later to, for example, approximately a drive voltage of 1.8 V±3% and applies it to the transmission cable 3, thereby feeding the drive power to the imaging device 20.

Under the control of the FPGA unit 51, the third power source IC 533 adjusts a voltage of a drive power input from the primary power source of the processor 6 described later to, for example, approximately a drive voltage of 1.2 V±3% and applies it to the transmission cable 3, thereby feeding the drive power to the imaging device 20.

The load unit 54 is provided between the power source unit 53 and the transmission lines T1 to T3, and consumes power equivalent to power to be consumed during an imaging period in which the imaging device 20 outputs the imaging signal. The load unit 54 includes: a first resistor R1 provided between the first power source IC 531 and the transmission line T1; a second resistor R2 provided between the second power source IC 532 and the transmission line T2; and a third resistor R3 provided between the third power source IC 533 and the transmission line T3.

One end of the first resistor R1 is connected to the first switch SW1 serving as the second switch unit described later, and the other end of the first resistor R1 is connected to the ground. Furthermore, the first resistor R1 may be a variable resistor of which the resistance value is variable under the control of the FPGA unit 51.

One end of the second resistor R2 is connected to the second switch SW2 serving as the second switch unit described later, and the other end of the second resistor R2 is connected to the ground. Furthermore, the second resistor R2 may be a variable resistor of which the resistance value is variable under the control of the FPGA unit 51.

One end of the third resistor R3 is connected to the third switch SW3 serving as the second switch unit described later, and the other end of the third resistor R3 is connected to the ground. Furthermore, the third resistor R3 may be a variable resistor of which the resistance value is variable under the control of the FPGA unit 51.

Under the control of the FPGA unit 51, the first switch SW1 connects the first resistor R1 to the transmission line T1 during a period other than the imaging period in which the imaging device 20 outputs the imaging signal. Specifically, under the control of the FPGA unit 51, the first switch SW1 connects the first resistor R1 to the transmission line T1 during a blanking period of the imaging device 20.

Under the control of the FPGA unit 51, the second switch SW2 connects the second resistor R2 to the transmission line T2 during a period other than the imaging period in which the imaging device 20 outputs the imaging signal. Specifically, under the control of the FPGA unit 51, the second switch SW2 connects the second resistor R2 to the transmission line T2 during a blanking period of the imaging device 20.

Under the control of the FPGA unit 51, the third switch SW3 connects the third resistor R3 to the transmission line T3 during a period other than the imaging period in which the imaging device 20 outputs the imaging signal. Specifically, under the control of the FPGA unit 51, the third switch SW3 connects the third resistor R3 to the transmission line T3 during a blanking period of the imaging device 20.

Configuration of the Processor

Next, the configuration of the processor 6 is explained. The processor 6 includes an image processing unit 61 and a primary power source unit 62.

The image processing unit 61 executes predetermined image processing on the imaging signal input from the endoscope 2 and outputs them to the display device 7. The image processing unit 61 is configured by using an FPGA, or the like. Here, as the predetermined image processing, at least basic image processing is conducted, including optical-black subtraction process, white spot correction process, black spot correction process, white balance adjustment process, demosaicing process on image data when the imaging device 20 has a Bayer arrangement, noise reduction process, color matrix calculation process, y correction process, color reproduction process, edge enhancement process, and the like.

The primary power source unit 62 boosts, or the like, an external power input from an external unit so as to have a predetermined voltage and outputs it to the power source unit 53 in the connector unit 5.

Operation of the Imaging Device

Figure 3:
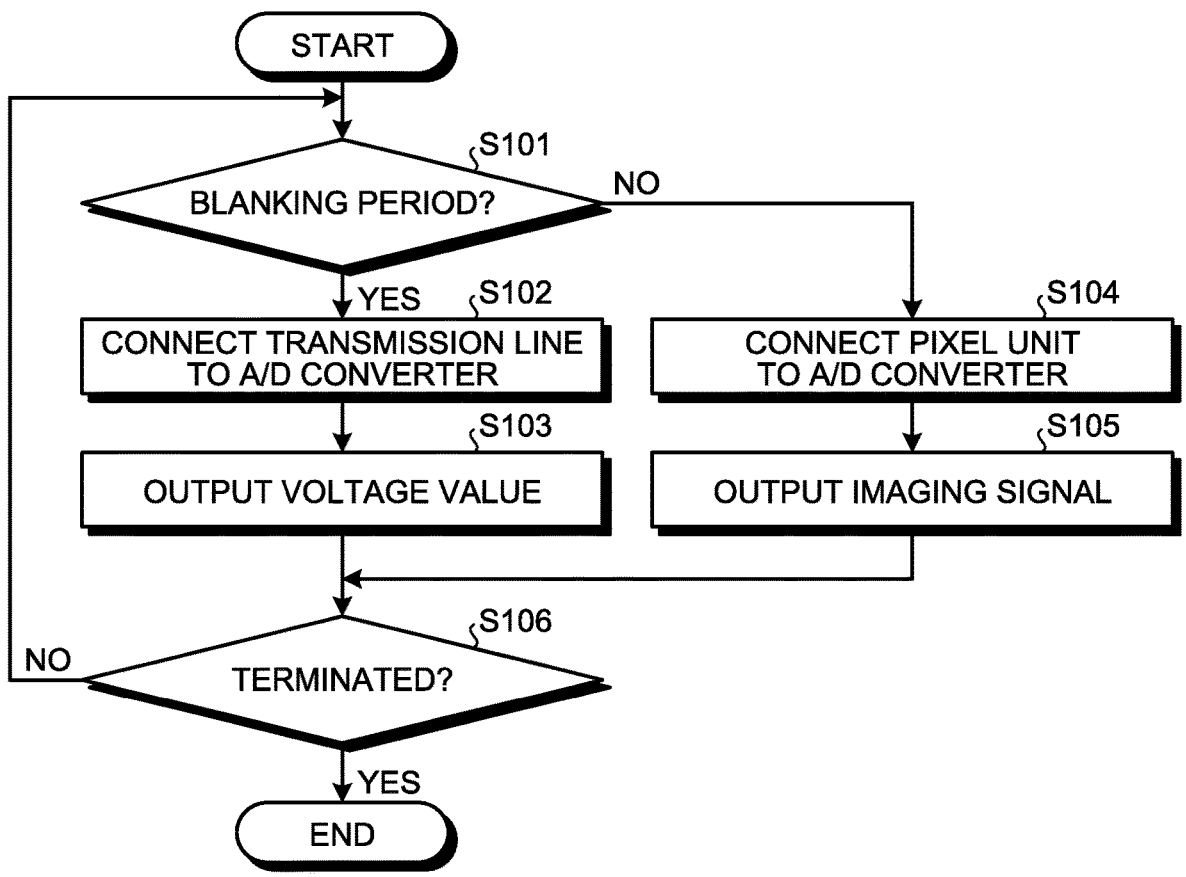
FIG. 3 is a flowchart that schematically illustrates an operational process performed by an imaging device according to the first embodiment of the present disclosure.

Next, operation of the imaging device 20 is explained. FIG. 3 is a flowchart that schematically illustrates an operational process performed by the imaging device 20.

As illustrated in FIG. 3, the timing generating unit 24 determines based on a clock signal input through the PLL 25 whether the imaging device 20 is in a blanking period (Step S101). When the timing generating unit 24 determines that the imaging device 20 is in a blanking period (Step S101: Yes), the imaging device 20 proceeds to Step S102 described later. Conversely, when the timing generating unit 24 determines that the imaging device 20 is not in a blanking period (Step S101: No), the imaging device 20 proceeds to Step S104 described later.

At Step S102, the timing generating unit 24 controls the switch unit 26 such that the transmission lines T1 to T3 for transmitting drive powers to drive the pixel unit 21 are connected to the A/D converter 27. Specifically, the timing generating unit 24 controls the switch unit 26 so as to switch the connection of the A/D converter 27 from the pixel unit 21 to the transmission lines T1 to T3 for transmitting drive powers.

Then, the timing generating unit 24 causes the A/D converter 27 to monitor the voltages of the drive powers transmitted from the transmission lines T1 to T3 so as to cause the A/D converter 27 to output the voltage value of the drive power of each of the transmission lines T1 to T3 to the signal processing unit 28 (Step S103). As a result, the signal processing unit 28 may output the voltage value of each of the drive powers monitored by the A/D converter 27 to the connector unit 5 through the transmission cable 3. After Step S103, the imaging device 20 proceeds to Step S106 described later.

At Step S104, the timing generating unit 24 controls the switch unit 26 such that the pixel unit 21 is connected to the A/D converter 27. Specifically, the timing generating unit 24 controls the switch unit 26 so as to switch the connection of the A/D converter 27 from the transmission lines T1 to T3 for transmitting drive powers to the pixel unit 21.

Then, the timing generating unit 24 causes the A/D converter 27 to output the imaging signal generated by the pixel unit 21 to the signal processing unit 28 (Step S105). This allows the signal processing unit 28 to output a digital imaging signal to the connector unit 5 through the transmission cable 3. After Step S105, the imaging device 20 proceeds to Step S106 described later.

Figure 4:
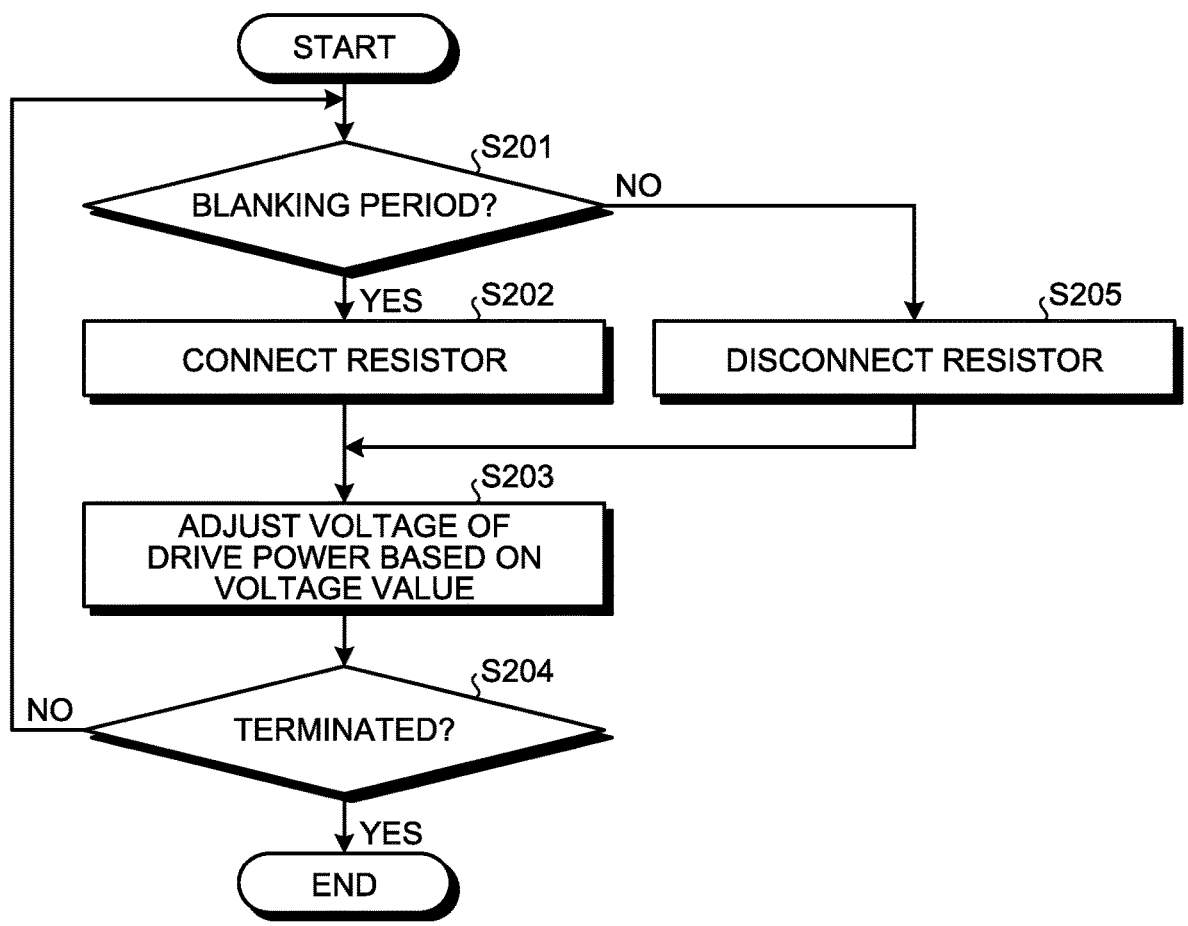
FIG. 4 is a flowchart that schematically illustrates an operational process performed by an FPGA unit according to the first embodiment of the present disclosure.

At Step S106, when imaging by the imaging device 20 is terminated (Step S106: Yes), the imaging device 20 terminates this process. Conversely, when imaging by the imaging device 20 is not terminated (Step S106: No), the imaging device 20 returns to Step S101 described above. Operation of the FPGA unit Next, a process performed by the FPGA unit 51 is explained. FIG. 4 is a flowchart that schematically illustrates an operational process performed by the FPGA unit 51.

As illustrated in FIG. 4, first, when the imaging device 20 is in a blanking period (Step S201: Yes), the FPGA unit 51 selects a connected state between the transmission lines T1 to T3, to which the power source unit 53 transmits drive powers, and the resistors (Step S202). Specifically, the FPGA unit 51 turns on the first switch SW1, the second switch SW2, and the third switch SW3. This results in the connection between the transmission lines T1 to T3, to which the power source unit 53 transmits drive powers, and the first resistor R1, the second resistor R2, and the third resistor R3, respectively, whereby power equivalent to power to be consumed in the imaging period of the imaging device 20 is consumed. As a result, an amount of power consumed in a drive state of the imaging device 20 is the same as an amount of power consumed in a non-drive state of the imaging device 20, which may prevent voltage depression in drive power so as to satisfy the accuracy of the voltage of a drive power needed by the imaging device 20 and may prevent deterioration in the imaging signal generated by the imaging device 20.

Then, the FPGA unit 51 adjusts the voltage of the drive power supplied by the power source unit 53 based on the voltage value of the drive power output from the imaging device 20 (Step S203). Specifically, the FPGA unit 51 controls voltages of drive powers to be adjusted by the first power source IC 531, the second power source IC 532, and the third power source IC 533, based on a average value of multiple voltage values output from the imaging device 20. This enables a satisfied accuracy of a voltage of a drive power needed by the imaging device 20 even when the length of the transmission cable 3 is changed due to assembly, repair, or the like.

Then, when observation by the endoscope system 1 is terminated (Step S204: Yes), the FPGA unit 51 terminates this process. Conversely, when observation by the endoscope system 1 is not terminated (Step S204: No), the FPGA unit 51 returns to Step S201 described above.

At Step S201, when the imaging device 20 is not in a blanking period (Step S201: No), the FPGA unit 51 selects a disconnected state between the transmission lines T1 to T3, to which the power source unit 53 transmits drive currents, and the resistors (Step S205). After Step S205, the FPGA unit 51 proceeds to Step S203.

According to the first embodiment of the present disclosure described above, a power having a satisfied voltage that is required is suppliable even when the length of the transmission cable 3 is changed due to assembly, repair, or the like.

Furthermore, according to the first embodiment of the present disclosure, the timing generating unit 24 controls the switch unit 26 such that transmission lines T1 to T3 are connected to the A/D converter 27 during a blanking period of the pixel unit 21 to cause the A/D converter 27 for the pixel unit 21 to output the voltage value of each drive power to an external unit, whereby detection circuitry for detecting the voltage value of a drive power does not need to be separately provided in the imaging device 20, the size of the imaging device 20 may be reduced, and even when the length of the transmission cable 3 is changed due to assembly, repair, or the like, information on a voltage value of a drive power (monitored value of the drive voltage) needed by the imaging device 20 may be output to the connector unit 5. As a result, a high-accuracy drive voltage needed by the imaging device 20 is suppliable.

Furthermore, according to the first embodiment of the present disclosure, the FPGA unit 51 adjusts voltages of drive powers to be supplied to the transmission lines T1 to T3 by the power source unit 53, based on the voltage value output from the imaging device 20, whereby the drive voltage required according to the specification of the power source of the imaging device 20 is suppliable with a high accuracy even when the length of the transmission cable 3 is changed due to assembly, repair, or the like.

Furthermore, according to the first embodiment of the present disclosure, with the FPGA unit 51, based on the average value of voltage values output from the imaging device 20, the drive voltage needed by the imaging device 20 is suppliable with a high accuracy even when the length of the transmission cable 3 is changed due to assembly, repair, or the like.

Furthermore, according to the first embodiment of the present disclosure, the FPGA unit 51 switches on the first switch SW1, the second switch SW2, and the third switch SW3 such that the transmission lines T1 to T3 are connected to the first resistor R1, the second resistor R2, and the third resistor R3 during a blanking period of the pixel unit 21, whereby fluctuations in consumed currents between a drive state and a non-drive state of the imaging device 20 may be reduced, the accuracy of the voltage of a drive power needed by the imaging device 20 may be satisfied, and therefore deterioration in imaging signals generated by the imaging device 20 may be prevented.

Although the timing generating unit 24 controls the switch unit 26 such that the transmission lines T1 to T3 are connected to the A/D converter 27 during a blanking period of the pixel unit 21 according to the first embodiment of the present disclosure, the switch unit 26 may be controlled such that the transmission lines T1 to T3 are connected to the A/D converter 27 during for example an optical-black output period for outputting an electric signal of a pixel provided in the pixel unit 21 for an optical black process. In this case, the FPGA unit 51 may perform a control to adjust the voltages of drive powers to be supplied to the transmission lines T1 to T3 by the power source unit 53, based on an average value of voltage values during a blanking period of the pixel unit 21 and on an average value of voltage values during an optical-black output period of the pixel unit 21.

Furthermore, although the timing generating unit 24 controls the switch unit 26 such that the transmission lines T1 to T3 are connected to the A/D converter 27 during a blanking period of the pixel unit 21 according to the first embodiment of the present disclosure, the switch unit 26 may be controlled such that the transmission lines T1 to T3 are connected to the A/D converter 27 during part of an imaging period of the pixel unit 21, for example, during part of an imaging period for outputting imaging signals in predetermined horizontal lines of effective pixels in the pixel unit 21, e.g., five lines from the uppermost end of the pixel unit 21. This enables detection of a voltage value of a drive power in the drive and non-drive states of the imaging device 20, whereby the drive voltage needed by the imaging device 20 is suppliable with a higher accuracy.

Furthermore, although the FPGA unit 51 performs a control to adjust the voltage of the drive power to be supplied to the transmission lines T1 to T3 by the power source unit 53, based on the average value of voltage values output from the imaging device 20 according to the first embodiment of the present disclosure, a control may be performed to adjust the voltage of the drive power to be supplied to the transmission lines T1 to T3 by the power source unit 53, based on for example an average value of voltage values during a blanking period of the pixel unit 21 and on an average value of voltage values during an imaging period of the pixel unit 21.

Furthermore, according to the first embodiment of the present disclosure, the transmission lines T1 to T3 are connected to the A/D converters 27, respectively; however, for example, when high power accuracy is required for a drive voltage, each of the transmission lines T1 to T3 may be connected to the A/D converters 27. For example, the transmission line T2 (a drive voltage of 1.8 V) may be connected to the A/D converters 27 to cause each of the A/D converters 27 to detect the voltage value of the drive power transmitted from the transmission line T2. In this case, the FPGA unit 51 may control the second power source IC 532 based on the voltage value of the transmission line T2, the voltage value of the transmission line T2 being an average value of voltage values.

Furthermore, according to the first embodiment of the present disclosure, when a power-supply voltage is monitored in a factory or a service facility, the timing generating unit 24 may monitor the voltage value of a drive power by controlling the switch unit 26 such that the transmission lines T1 to T3 are connected to the A/D converter 27 during a first half period of an imaging period of the pixel unit 21. In this case, a user may conduct it while changing an object to further improve accuracy. Here, it is obvious that the FPGA unit 51 may control the power source unit 53 by using an average value of voltage values.

Furthermore, although the FPGA unit 51 uses an average value of voltage values according to the first embodiment of the present disclosure, for example, the middle value, the mode value, the minimum value, the maximal value, the weighted average value, or the like, other than the average value may be used. It is obvious that the FPGA unit 51 may compare a voltage value output from the imaging device 20 with a preset threshold and, according to a comparison result (for example, less than the threshold), control the power source unit 53. Furthermore, the FPGA unit 51 may determine whether a voltage value output from the imaging device 20 falls within an acceptable range and control the power source unit 53 when it falls out of the acceptable range.

Second Embodiment

Next, the second embodiment of the present disclosure is explained. The second embodiment is different from the above-described first embodiment in the configuration of the imaging device 20 and a process performed.

Specifically, although the A/D converter 27, which conducts A/D conversion on imaging signals of the pixel unit 21, monitors the voltage value of the drive power for driving the pixel unit 21 and outputs the voltage value to an external unit according to the above-described first embodiment, a new A/D converter that monitors the voltage value of a drive power is separately provided to output the voltage value to an external unit in predetermined timing according to the second embodiment. After the configuration of an endoscope system according to the second embodiment is explained below, a process performed by an imaging device according to the second embodiment is explained. Furthermore, the same configuration as that in the endoscope system 1 according to the above-described first embodiment is attached with the same reference numeral, and its explanation is omitted.

Configuration of an Endoscope System

Figure 5:
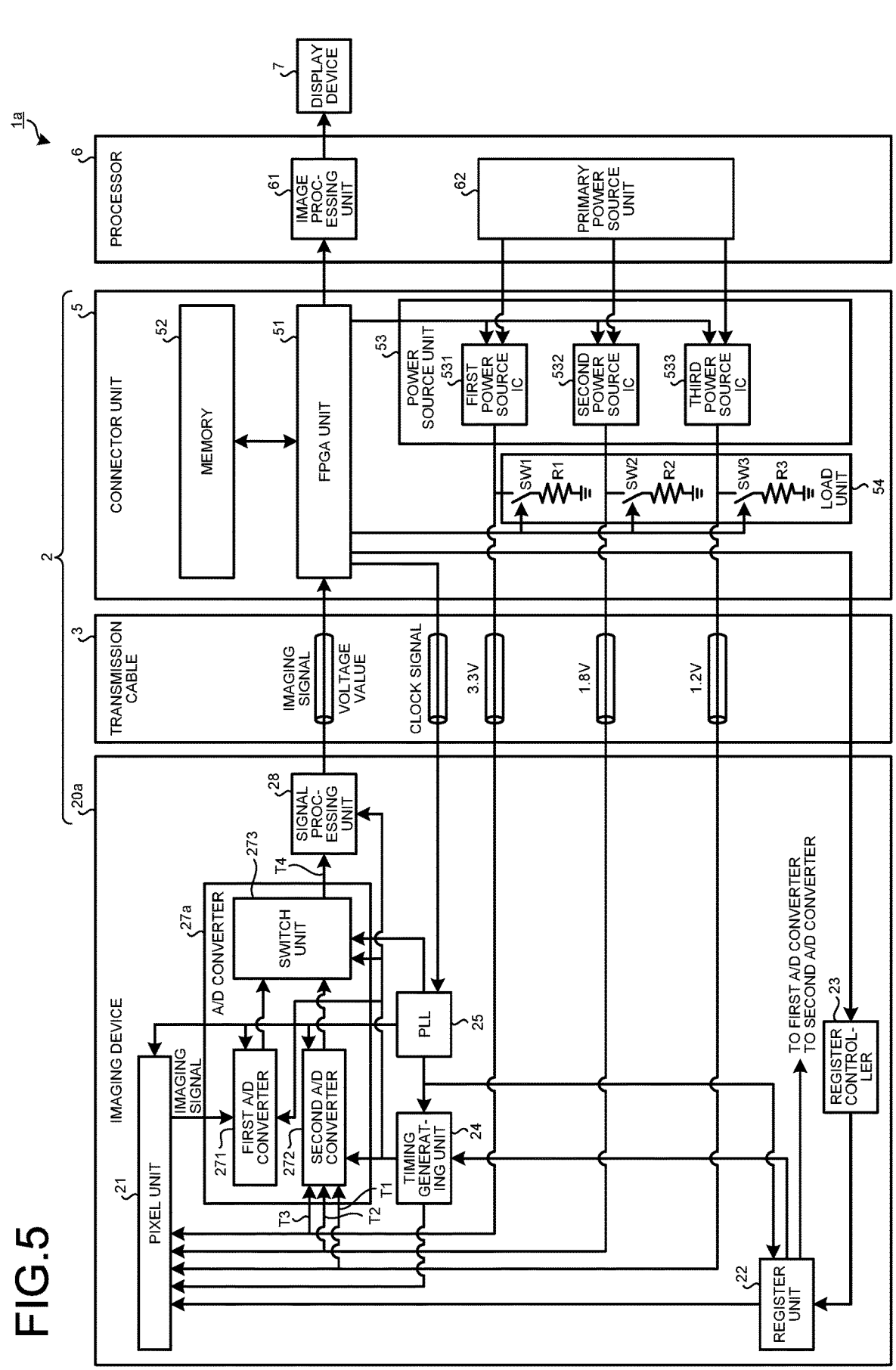
FIG. 5 is a block diagram that illustrates the function of a relevant part of an endoscope system according to a second embodiment of the present disclosure.

FIG. 5 is a block diagram that illustrates the function of a relevant part of the endoscope system according to the second embodiment. An endoscope system 1a illustrated in FIG. 5 includes an imaging device 20a instead of the imaging device 20 in the endoscope system 1 according to the above-described first embodiment.

Configuration of the Imaging Device

The imaging device 20a illustrated in FIG. 5 includes an A/D converter 27a instead of the A/D converter 27 according to the above-described first embodiment. Furthermore, the switch unit 26 according to the above-described first embodiment is omitted from the imaging device 20a.

The A/D converter 27a conducts A/D conversion on the imaging signal generated by the pixel unit 21 or on the drive power for driving the pixel unit 21, input from an external unit, to generate a digital signal and outputs the digital imaging signal to an external unit. The A/D converter 27a includes a first A/D converter 271, a second A/D converter 272, and a switch unit 273.

The first A/D converter 271 conducts A/D conversion on the imaging signal input from the pixel unit 21 to generate a digital signal and outputs digital imaging signals to the switch unit 273.

The second A/D converter 272 connects to the transmission lines T1 to T3 for transmitting drive powers based on clock signals input from the timing generating unit 24. The second A/D converter 272 conducts A/D conversion on drive powers (monitors each drive voltage (3.3 V, 1.8 v, 1.2 V)), based on clock signals input from the timing generating unit 24, thereby outputting digital voltage values (monitored values) of the drive powers to the switch unit 273. Furthermore, the second A/D converter 272 may include a plurality of A/D converters where each A/D converter corresponds to each one of the transmission lines T1 to T3, or may include a switch that is provided between the second A/D converter 272 and the transmission lines T1 to T3 and that is sequentially changed in a predetermined cycle to connect the second A/D converter 272 to each of the transmission lines T1 to T3.

The switch unit 273 is connected to the first A/D converter 271 and the second A/D converter 272, and is configured to connect an output of any one of the first A/D converter 271 and the second A/D converter 272 to an external transmission line T4 for transmitting signals to an external unit. Specifically, based on clock signals input from the timing generating unit 24, the switch unit 273 that is connected to the first A/D converter 271 and the second A/D converter 272 connects the output of any one of the first A/D converter 271 and the second A/D converter 272 to the external transmission line T4 for transmitting signals to an external unit. The switch unit 273 is implemented by using a semiconductor switch, such as PMOS or NMOS, a mechanical switch, or the like.

Operation of the Imaging Device

Figure 6:
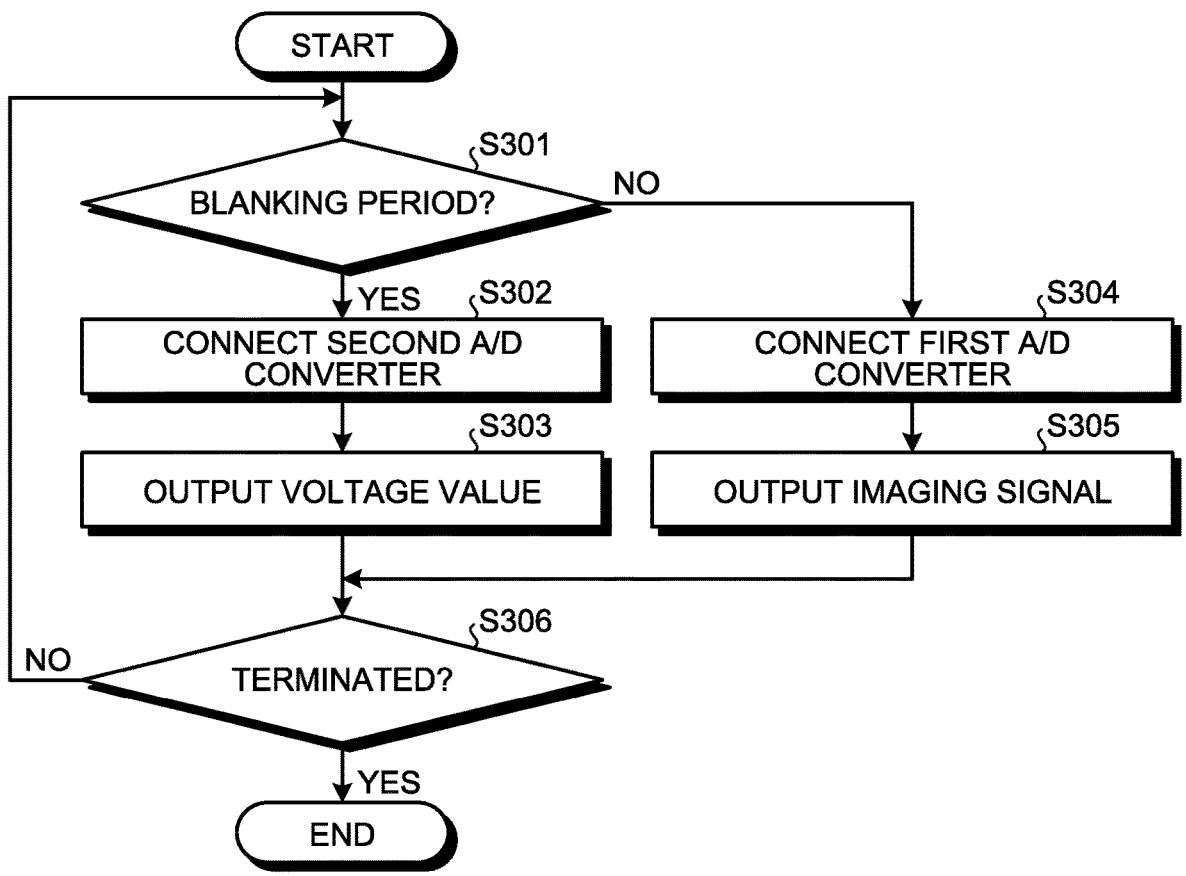
FIG. 6 is a flowchart that schematically illustrates an operational process performed by an imaging device according to the second embodiment of the present disclosure.

Next, operation of the imaging device 20a is explained. FIG. 6 is a flowchart that schematically illustrates an operational process performed by the imaging device 20a.

As illustrated in FIG. 6, the timing generating unit 24 determines based on a clock signal input through the PLL 25 whether the imaging device 20a is in a blanking period (Step S301). When the timing generating unit 24 determines that the imaging device 20a is in a blanking period (Step S301: Yes), the imaging device 20a proceeds to Step S302 described later. Conversely, when the timing generating unit 24 determines that the imaging device 20a is not in a blanking period (Step S301: No), the imaging device 20a proceeds to Step S304 described later.

At Step S302, the timing generating unit 24 controls the switch unit 273 such that the second A/D converter 272 is connected to the external transmission line T4. Specifically, the timing generating unit 24 controls the switch unit 273 such that the second A/D converter 272 is connected to the signal processing unit 28.

Then, the timing generating unit 24 causes the second A/D converter 272 to conduct A/D conversion on voltages of drive powers transmitted from the transmission lines T1 to T3 for monitoring and output digital voltage values monitored to the signal processing unit 28 (Step S303). As a result, the signal processing unit 28 may output a voltage value of each drive power monitored by the second A/D converter 272 through the external transmission line T4, which is part of the transmission cable 3, to the connector unit 5. After Step S303, the imaging device 20a proceeds to Step S306 described later.

At Step S304, the timing generating unit 24 controls the switch unit 273 such that the first A/D converter 271 is connected to the external transmission line T4. Specifically, the timing generating unit 24 controls the switch unit 273 such that the first A/D converter 271 is connected to the signal processing unit 28.

Then, the timing generating unit 24 causes the first A/D converter 271 to conduct A/D conversion on the imaging signal input from the pixel unit 21 to output a digital imaging signal to the signal processing unit 28 (Step S305). As a result, the signal processing unit 28 may output the digital imaging signal generated by the first A/D converter 271 through the external transmission line T4, which is part of the transmission cable 3, to the connector unit 5. After Step S305, the imaging device 20a proceeds to Step S306 described later.

At Step S306, when imaging by the imaging device 20a is terminated (Step S306: Yes), the imaging device 20a terminates this process. Conversely, when imaging by the imaging device 20a is not terminated (Step S306: No), the imaging device 20a returns to Step S301 described above.

The above-described second embodiment of the present disclosure produces an advantage similar to that of the above-described first embodiment so as to supply a power having a satisfied voltage that is required even when the length of the transmission cable 3 is changed due to assembly, repair, or the like.

Furthermore, according to the second embodiment of the present disclosure, the timing generating unit 24 controls the switch unit 273 such that the second A/D converter 272 is connected to the external transmission line 14 in predetermined timing; therefore, even when the length of the transmission cable 3 is changed due to assembly, repair, or the like, information on the voltage value of the drive power (the monitored value of the drive voltage) needed by the imaging device 20a may be output to the connector unit 5. As a result, the drive voltage needed by the imaging device 20a is suppliable with a high accuracy.

Furthermore, according to the second embodiment of the present disclosure, the second A/D converter 272 that monitors only a voltage value of a drive power is provided in addition to the first A/D converter 271 that conducts A/D conversion on an image signal, whereby effects of noise in drive power on the imaging signal may be prevented.

Furthermore, according to the second embodiment of the present disclosure, although the timing generating unit 24 causes the second A/D converter 272 to output the monitored voltage value of the drive power to an external unit during a blanking period of the pixel unit 21, it may cause the second A/D converter 272 to output the monitored voltage value of the drive power to an external unit during an optical-black output period for outputting an electric signal of a pixel provided in the pixel unit 21 for an optical black process.

Furthermore, according to the second embodiment of the present disclosure, although the timing generating unit 24 causes the second A/D converter 272 to output the monitored voltage value of the drive power to an external unit during a blanking period of the pixel unit 21, it may cause the second A/D converter 272 to output the monitored voltage value of the drive power to an external unit during part of an imaging period of the pixel unit 21, for example, during part of an imaging period for outputting imaging signals in predetermined horizontal lines of effective pixels in the pixel unit 21, e.g., five lines from the uppermost end of the pixel unit 21. This allows detection of a voltage value of a drive power in the drive and non-drive states of the imaging device 20*a*, whereby the drive voltage needed by the imaging device 20*a* is suppliable with a higher accuracy.

Other Embodiments

Furthermore, according to the embodiment of the present disclosure, although the processor 6 and the light source device 8 are separate, this is not a limitation, and for example the processor 6 and the light source device 8 may be integrally formed.

Furthermore, according to the embodiment of the present disclosure, although the simultaneous lighting endoscope is explained as an example, a sequential lighting endoscope is also applicable.

Furthermore, according to the embodiment of the present disclosure, although the imaging device 20 is explained as a color filter having a Bayer arrangement, for example a complementary filter and a laminated filter are also applicable.

Furthermore, for example a capsule endoscope, an imaging device that captures a subject, and a monitoring camera that conducts imaging through a signal cable are also applicable other than the endoscope configured to be inserted into a subject according to the embodiment of the present disclosure.

Furthermore, according to the embodiment of the present disclosure, rigid endoscopes, sinus endoscopes, and electric cauteries, or examination probes, which are medical apparatuses that need take measures for electromagnetic compatibility (Electromagnetic Compatibility: EMC), are also applicable other than flexible endoscopes (upper and lower endoscope scopes).

According to the present disclosure, there is an advantage such that, even when the length of a signal cable is changed, a power having a satisfied power-supply voltage needed by an imaging device is suppliable.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
    a pixel unit including a plurality of pixels that are arranged in a two-dimensional matrix, each pixel being configured to generate an imaging signal corresponding to an amount of light received and output the image signal;
    an A/D converter configured to conduct A/D conversion on the imaging signal generated by the pixel unit or on a drive power that is an external input and that is used for driving the pixel unit, to generate a digital signal and output the digital signal to an external unit;
    a switch that is capable of switching a connection of the A/D converter to the pixel unit or a transmission line for transmitting the drive power; and
    a first controller configured to control the switch to connect the A/D converter to the transmission line in predetermined timing to cause the A/D converter to output a voltage value of the drive power to the external unit.

2. The imaging device according to claim 1, wherein the first controller is configured to:
    control the switch to connect the A/D converter to the transmission line during a blanking period or an optical-black output period of the pixel unit; and
    control the switch to connect the A/D converter to the pixel unit during an imaging period in which the pixel unit outputs the imaging signal.

3. The imaging device according to claim 1, wherein the first controller is configured to control the switch to connect the A/D converter to the transmission line during part of an imaging period in which the pixel unit outputs the imaging signal.

4. An endoscope comprising:
    the imaging device according to claim 1;
    a power source configured to adjust a voltage of an external power input from a processor to be supplied as the drive power; and
    a second controller that controls a voltage of the drive power to be adjusted by the power source, based on the voltage value.

5. The endoscope according to claim 4, wherein the second controller is configured to control a voltage of the drive power to be adjusted by the power source, based on an average value of voltage values.

6. The endoscope according to claim 4, further comprising:
    a load that is capable of consuming power that is equivalent to power to be consumed in an imaging period in which the pixel unit outputs the imaging signal; and
    a second switch that is connected to the load and connectable to a transmission line for transmitting the drive power, wherein
    the second controller is configured to control the second switch to connect the load to the transmission line during a blanking period of the pixel unit.

7. The endoscope according to claim 6, further comprising:
    an insertion portion configured to be inserted into a subject; and
    a proximal end portion that is attachable to and detachable from the processor, wherein
    the imaging device is provided at a distal end portion of the insertion portion, and
    the power source, the load, the second switch, and the second controller are provided at the proximal end portion.

8. An imaging device comprising:
    a pixel unit including a plurality of pixels that are arranged in a two-dimensional matrix, each pixel being configured to generate an imaging signal corresponding to an amount of light received and output the image signal;
    an A/D converter configured to conduct A/D conversion on the imaging signal generated by the pixel unit or on a drive power that is an external input and that is used for driving the pixel unit, to generate a digital signal and output the digital signal to an external unit; and
    a first controller configured to cause the A/D converter to output a voltage value of the drive power to the external unit in predetermined timing, wherein
    the A/D converter includes:
        a first A/D converter that is connected to the pixel unit, the first A/D converter being configured to conduct A/D conversion on the imaging signal to generate a digital imaging and output the digital imaging signal to the external unit;

a second A/D converter that is connected to a transmission line for transmitting the drive power, the second A/D converter being configured to conduct A/D conversion on the drive power to output a digital voltage value of the drive power to the external unit; and a switch that is connected to the first A/D converter and the second A/D converter, the switch being configured to connect an output of any one of the first A/D converter and the second A/D converter to an external transmission line for transmitting a signal to the external unit, and the first controller is configured to control the switch to connect the second A/D converter to the external transmission line in predetermined timing.

9. The imaging device according to claim 8, wherein the first controller is configured to:

control the switch to connect the second A/D converter to the external transmission line during a blanking period or an optical-black output period of the pixel unit; and control the switch to connect the first A/D converter to the external transmission line during an imaging period in which the pixel unit outputs the imaging signal.

10. The imaging device according to claim 8, wherein the first controller is configured to control the switch to connect the second A/D converter to the external transmission line during part of an imaging period in which the pixel unit outputs the imaging signal.

\* \* \* \* \*